US012138359B2

(12) United States Patent
Thiessen et al.

(10) Patent No.: US 12,138,359 B2
(45) Date of Patent: Nov. 12, 2024

(54) GRAIN TREATMENT APPARATUS USING OZONE

(71) Applicants: Roland Dean Thiessen, Portage la Prairie (CA); Lonny James Thiessen, Portage la Prairie (CA)

(72) Inventors: Roland Dean Thiessen, Portage la Prairie (CA); Lonny James Thiessen, Portage la Prairie (CA)

(*) Notice: Subject to any disclaimer, the term of this patent is extended or adjusted under 35 U.S.C. 154(b) by 397 days.

(21) Appl. No.: 17/691,655

(22) Filed: Mar. 10, 2022

(65) Prior Publication Data

US 2022/0288260 A1     Sep. 15, 2022

Related U.S. Application Data

(60) Provisional application No. 63/161,137, filed on Mar. 15, 2021.

(51) Int. Cl.
| | | |
|---|---|---|
| *A61L 2/20* | (2006.01) | |
| *A01F 25/14* | (2006.01) | |
| *B65G 65/22* | (2006.01) | |

(52) U.S. Cl.
CPC ............. *A61L 2/202* (2013.01); *A01F 25/14* (2013.01); *B65G 65/22* (2013.01); *B65G 2201/042* (2013.01)

(58) Field of Classification Search
CPC .......... A61L 2/202; A61L 2/183; A01F 25/14; B65G 65/22; B65G 2201/042; B65G 33/26; B65G 65/463; B65G 65/32; B65G 65/34; B65G 65/42; A23B 7/144; A23B 9/18; A23L 3/3409; A23L 5/27; B65D 88/14; B65D 88/544; B65D 88/30; B65D 2588/12; B65D 2588/05; B65D 88/32; B65D 88/12; B60P 1/483; B60P 3/00; B60P 1/6427; B60P 1/6418; B01F 35/883; B01F 35/2112; B01F 2101/49; G05D 11/132; E21B 43/267; E04H 7/22; B02C 18/2216; B02C 25/00; B02C 23/20; B02C 19/0075;
(Continued)

(56) References Cited

U.S. PATENT DOCUMENTS

| | | | | |
|---|---|---|---|---|
| 6,120,822 A | * | 9/2000 | Denvir | ............... A23B 9/18 99/473 |
| 2018/0070601 A1 | * | 3/2018 | Lepez | ............... A23B 7/144 |

(Continued)

FOREIGN PATENT DOCUMENTS

KR            101408268        7/2014

*Primary Examiner* — Xiuyu Tai
(74) *Attorney, Agent, or Firm* — Ryan W. Dupuis; Kyle R. Satterthwaite; Ade & Company Inc.

(57) ABSTRACT

An ozone treatment apparatus for grain uses first and second storage bins and an auger conveyor for conveying the grain from a first end in communication with the bottom of the first bin to a second end that can be directed into either one of the top of the first bin or the top of the second bin. An ozone injector injects ozone into the auger conveyor for mixing with and treating the conveyed grain. In a first mode, the conveyor discharges the grain from the second end of the conveyor through a first discharge outlet into the first storage bin to recycle the grain during treatment. In a second mode, the conveyor discharges the grain through a second discharge outlet into the second storage bin once treatment is complete.

14 Claims, 2 Drawing Sheets

(58) Field of Classification Search
CPC ... B02C 23/02; B02C 2023/165; B02C 23/16; B09B 3/0075
See application file for complete search history.

(56) References Cited

U.S. PATENT DOCUMENTS

2020/0316660 A1* 10/2020 Jude .................... B02C 18/2216
2021/0276793 A1*  9/2021 Ford .................... B65D 88/14

* cited by examiner

GRAIN TREATMENT APPARATUS USING OZONE

This application claims the benefit under 35 U.S.C.119(e) of U.S. provisional application Ser. No. 63/161,137, filed Mar. 15, 2021.

FIELD OF THE INVENTION

The present invention relates to an apparatus for storing and treating a particulate material, for example grain, using ozone injected into an auger conveyor that conveys the grain to treat the grain while it is recycled within a storage bin or transferred between storage bins.

BACKGROUND

It is known that stored grain can become spoiled due to the presence of various pathogens and that it is desirable to condition or treat the grain by various means to minimize the damage to the grain by such pathogens. In some instance, the application of ozone has been known to inactive various pathogens in grain.

Korean Patent Application No. 101408268 by Lee Bea Sung describes a Grain Sterilizing Apparatus using Ozone Gas that is capable of sterilizing grains and nuts which are processed industrially in bulk, by putting ozone gas into a cylindrical grain transfer pipe equipped with a transfer auger sterilizing the grains by the ozone gas while the grains pass through the grain transfer pipe. This arrangement provides limited control over the amount of treatment and dwell time of the grain being exposed to the ozone.

SUMMARY OF THE INVENTION

According to one aspect of the invention there is provided a treatment apparatus for treating grain with ozone from a source of ozone, the apparatus comprising:
  a first storage bin arranged to contain a portion of the grain therein;
  a second storage bin in proximity to the first storage bin, the second storage bin being arranged to contain a portion of the grain therein;
  an auger conveyor arranged to convey the grain longitudinally through the auger conveyor from a first end to a second end of the auger conveyor, the first end of the auger conveyor being in communication with a bottom end of the first storage bin to receive the grain into the first end of the auger conveyor from the first storage bin; and
  an ozone injector arranged to inject ozone from the ozone source into the auger conveyor such that the grain conveyed by the auger conveyor is treated by the ozone;
  the auger conveyor including a first discharge outlet in association therewith, the first discharge outlet being in communication with the first storage bin adjacent a top end of the first storage bin;
  the auger conveyor including a second discharge outlet in association therewith, the second discharge outlet being in communication with the second storage bin adjacent a top end of the second storage bin;
  the auger conveyor being selectively operable in either one of a first mode or a second mode;
  in the first mode, the auger conveyor being arranged to discharge the grain through the first discharge outlet into the first storage bin; and
  in the second mode, the auger conveyor being arranged to discharge the grain through the second discharge outlet into the second storage bin.

Providing an auger conveyor that can treat conveyed grain with ozone while conveying grain in either one of a first mode to recycle the grain in the first bin or a second mode to transfer the grain to a second bin provides a great degree of flexibility and control over the treatment time of the grain and the number of treatments the grain undergoes to maximize the benefits of grain treatment using ozone.

The first end of the auger conveyor is preferably supported within the first storage bin.

The first storage bin may comprise a hopper bottom having a sloped bottom wall tapering towards a central discharge gate, in which the first end of the auger conveyor is located within a boundary of the sloped bottom wall of the hopper bottom at a location spaced above the central discharge gate of the hopper bottom.

The auger conveyor may extend longitudinally through a top end of the first storage bin from the first end of the auger conveyor within the first storage bin to a second end of the auger conveyor above the first storage bin.

The ozone injector may be in communication with the auger conveyor at an intermediate location nearer to the first end than the second end of the auger conveyor. More preferably, the ozone injector is in communication with the auger conveyor in proximity to the first end of the auger conveyor.

The auger conveyor is preferably driven by an auger motor supported at the second end of the auger conveyor, externally of the first and second storage bins.

When the auger conveyor includes an auger rotating within an auger housing, one of the discharge outlets may comprise an intermediate outlet at an intermediate location spaced from the second end of the auger conveyor and one of the discharge outlets may comprise a distal outlet at the second end of the auger conveyor.

The auger conveyor may further comprise a gate operable relative to the intermediate outlet between a closed position blocking the intermediate outlet so as to discharge the grain through the distal outlet according to one of the modes of the auger conveyor and an open position allowing discharge of grain through the intermediate outlet according to another one of the modes of the auger conveyor.

The auger conveyor may comprises: (i) a conveyor housing; (ii) a conveyor auger rotatably supported within the conveyor housing to convey the grain along the conveyor housing; (iii) the intermediate outlet comprising one or more outlet openings formed in the conveyor housing; and (iv) the gate comprising a collar supported for sliding movement relative to the conveyor housing between the closed position spanning across the one or more outlet openings in the conveyor housing and the open position in which the one or more outlet openings are at least partly unobstructed by the collar.

Preferably the intermediate outlet is the first discharge outlet in communication with the first storage bin and the distal outlet is the second discharge outlet in communication with the second storage bin. The first discharge outlet may be situated within an interior of the first storage bin.

The apparatus may include (i) a first discharge chute arranged to discharge grain therethrough by gravity from the first discharge outlet to a top end of the first storage bin, and/or (ii) a second discharge chute arranged to discharge grain therethrough by gravity from the second discharge outlet to a top end of the second storage bin.

According to a second aspect of the present invention there is provided a method of treating grain using ozone from a source of ozone, the method comprising:

placing the grain in a first storage bin;

conveying the grain using an auger conveyor from a bottom end to a top end of the first storage bin according to a first mode of operation of the auger conveyor;

transferring the grain using said auger conveyor from a bottom end of the first storage bin into a top end of a second storage bin according to a second mode of operation of the auger conveyor; and during operation of the auger conveyor in at least one of the first mode of operation or the second mode of operation, injecting ozone from the source of ozone into the auger conveyor such that the grain conveyed by the auger is treated with the ozone.

The method may further include injecting the ozone into the auger conveyor (i) only during the first mode of operation, (ii) only during the second mode of operation, or (iii) during both modes of operation.

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

Figure 1:
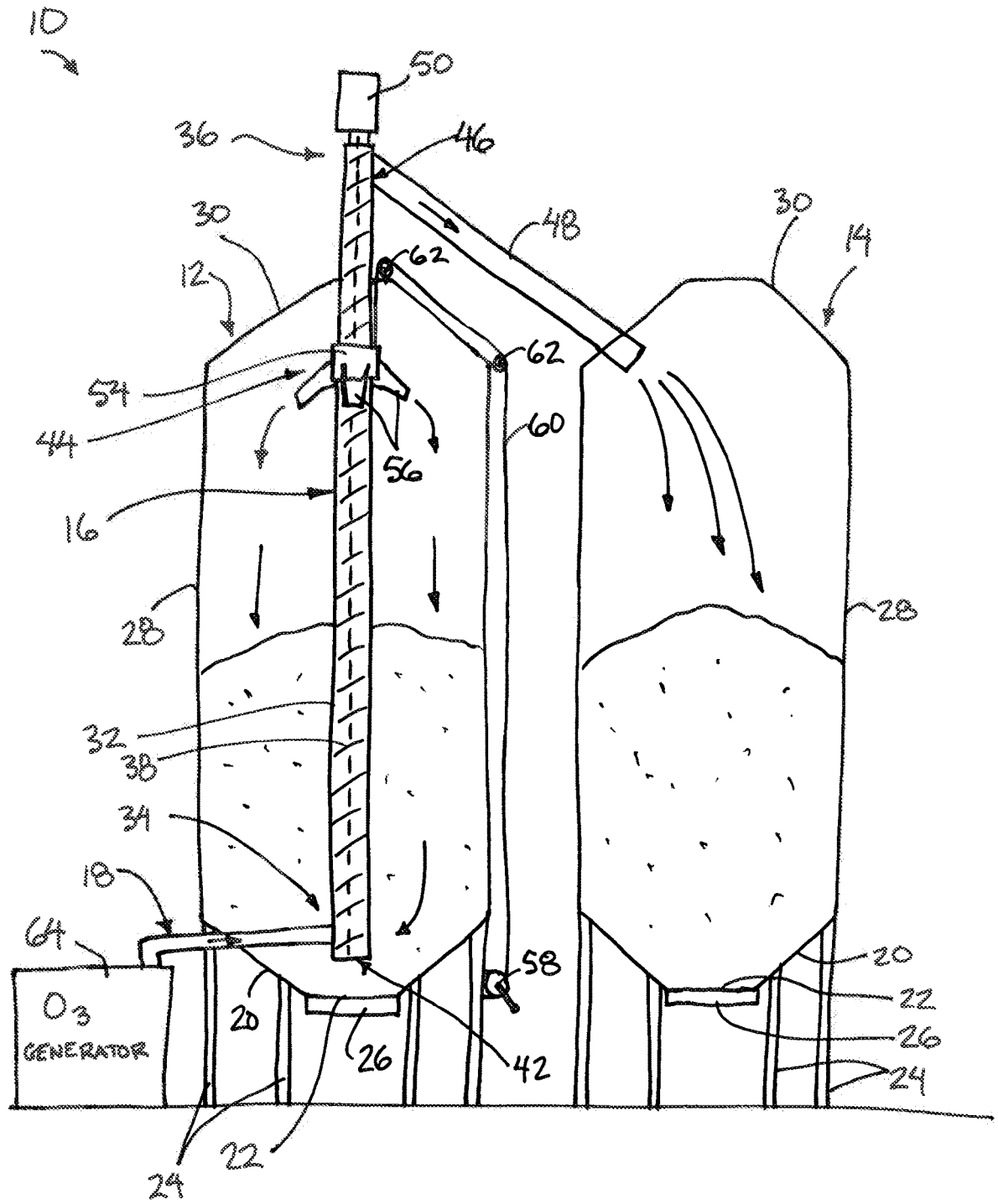
FIG. 1 is an elevational view of the treatment apparatus according to the present invention for operation in either one of a first mode to treat grain with ozone while it is recycled within a first storage bin or a second mode to optionally treat grain while it is transferred from the first storage bin to the second storage bin.
Figure 2:
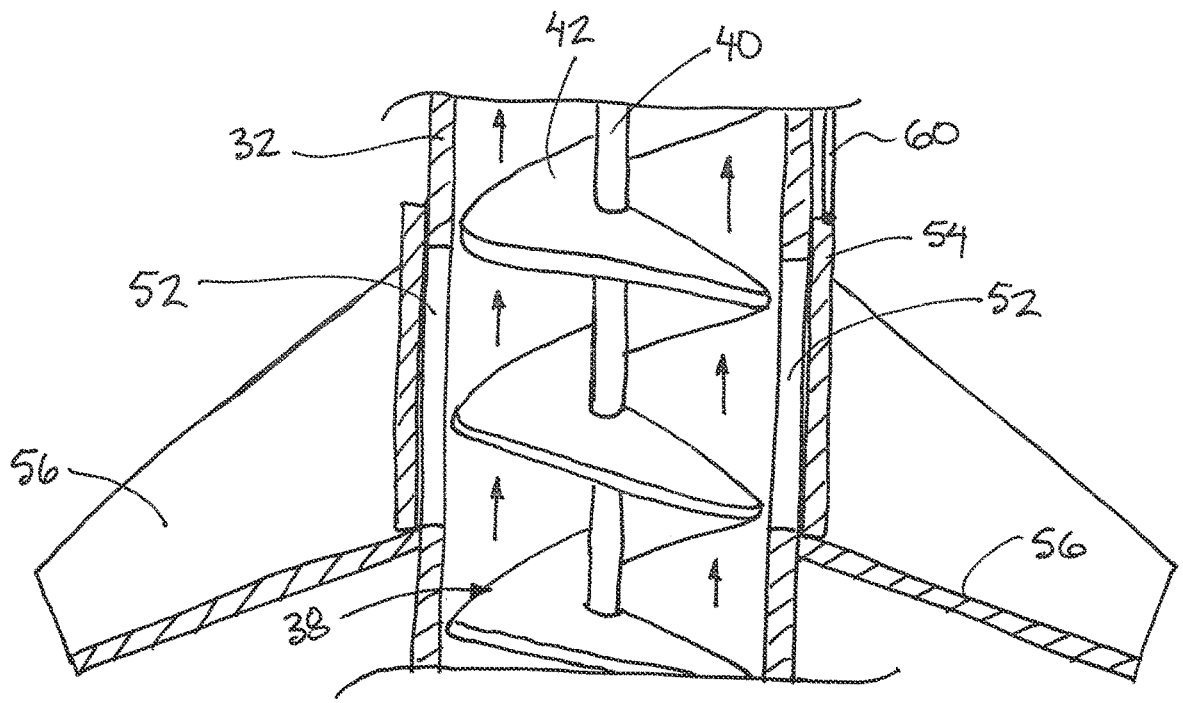
FIG. 2 is a sectional view of a gate on the auger conveyor of the apparatus according to FIG. 1 in a closed position according to the second mode of operation.
Figure 3:
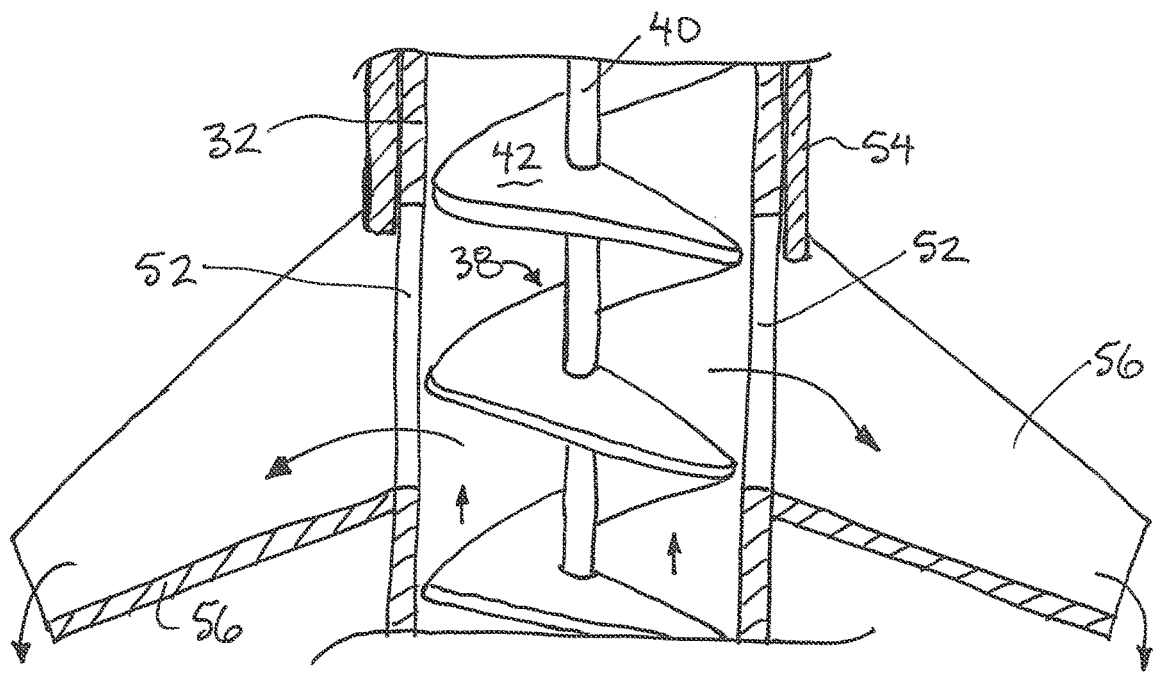
FIG. 3 is a sectional view of a gate on the auger conveyor of the apparatus according to FIG. 1 in an open position according to the first mode of operation.

Referring to the accompanying figures there is illustrated a grain treatment apparatus generally indicated by reference numeral 10. The apparatus 10 is particularly suited for treating grain with ozone.

The apparatus 10 generally includes (i) a first storage bin 12 arranged to contain at least a portion of the grain therein, (ii) a second storage bin 14 arranged to contain another portion of the grain therein, (iii) an auger conveyor 16 for conveying the grain in a manner that recycles grain within the first storage bin according to a first mode of operation or transfer grain from the first storage bin to the second storage bin according to a second mode of operation, and (iv) an ozone injector 18 for injecting ozone from a source of ozone into the auger conveyor for mixing with and treating the grain being conveyed with ozone.

The first storage bin 12 includes a hopper bottom 20 formed of a conical bottom wall that tapers downwardly and inwardly to a central bottom discharge opening 22. A plurality of upright legs 24 are fixed about the upper perimeter edge of the hopper bottom to extend downwardly therefrom and support the conical bottom wall spaced above the ground so as to be arranged to receive suitable handling equipment below the bottom discharge opening 22 if required. A bottom gate 26 is operatively connected to the bottom discharge opening 22 for operation between a closed position spanning across the opening to contain material within the bin and an open position in which the bottom discharge opening is substantially unobstructed to allow discharge of material from the bin through the bottom discharge opening.

The first storage bin 12 further includes a cylindrical boundary wall 28 extending upwardly from the upper perimeter edge of the hopper bottom 20 so as to be supported on the legs 24 of the bin. A top wall 30 forms an upper boundary of the first storage bin by spanning across a top end of the cylindrical boundary wall 28 at the top end of the storage bin.

The second storage bin 14 is substantially identical in structure to the first bin so as to similarly comprise (i) a hopper bottom 20 supported on legs 24 with a bottom gate 26 enclosing the bottom of the hopper bottom, and (ii) a cylindrical wall 28 and top wall 30 forming the side and top boundaries of the second storage bin. The second storage bin 14 may be identical in height and storage volume as the first storage bin 12.

The auger conveyor 16 includes a cylindrical and tubular conveyor housing 32 which is elongate and linear to span the full length of the conveyor between a first end 34 at the bottom of the conveyor and a second end 36 at the top end of the conveyor. A screw auger 38 is rotatably supported within the conveyor housing. The auger 38 comprises a shaft 40 and a helical flighting 42 mounted about the shaft to extend along the full length of the conveyor housing. The auger 38 is supported for rotation within the housing to convey particulate material along the conveyor from the first and to the second end thereof in the usual manner of an auger conveyor.

The auger conveyor 16 is mounted to be primarily situated within the first storage bin 12 to extend in a substantially vertical orientation from the first end 34 of the conveyor that is centrally located within the boundaries of the hopper bottom 20 of the storage bin to the second end 36 of the auger conveyor which terminates at a location spaced above the top end of the first storage bin 12, externally of the first storage bin. The conveyor housing 32 includes an intake opening 42 at the first end 34 thereof which is situated adjacent a bottom end of the first storage bin, spaced slightly above the bottom gate 26 of the hopper bottom 20 so as not to interfere with discharge of material through the bottom discharge opening 22 when desired.

The auger conveyor 16 further includes an intermediate outlet 44 communicating through the conveyor housing 32 at an intermediate location spaced longitudinally from both the first and second ends of the housing so as to be adjacent to a top end of the first storage bin within the interior of the storage bin. The intermediate outlet 44 thus defines a first discharge outlet in communication with the top end of the first storage bin. The auger conveyor 16 is arranged to discharge the conveyed material through the immediate outlet 44 into the top end of the first storage bin according to the first mode of operation of the auger conveyor as described in further detail below.

The auger conveyor 16 further includes a distal outlet 46 formed in the conveyor housing 32 at the second end of the conveyor housing 32 corresponding to a location at the exterior of the first storage bin, spaced above the top ends of both the first and second storage bins in the elevation. A distal discharge chute 48 communicates from the distal outlet 46 to a top end of the second bin. The distal outlet 46 may comprise an opening formed in a sidewall of the housing 32 of the auger conveyor in open communication with the distal discharge chute so that all material conveyed to the second end of the conveyor is discharged through the distal outlet into the discharge chute 48.

The distal discharge chute 48 is sloped downwardly and radially outward from the upright axis of the auger conveyor 16 to the top end of the second storage bin at a slope which is sufficiently near vertical to prevent accumulation of material within the chute so that any material deposited into the chute falls under action of gravity alone into the top end of the second storage bin. In this manner, the distal outlet 46 thus defines a second discharge outlet in communication with the top end of the second storage bin. The auger conveyor 16 is arranged to discharge the conveyed material through the distal outlet 46 into the top end of the second storage bin according to the second mode of operation of the auger conveyor as described in further detail below.

The auger conveyor 16 further includes a drive motor 50 supported externally of the conveyor housing 32 at the second end or top end thereof at a location externally of the first storage bin. The drive motor 50 comprises any suitable form of motor used for driving rotation of an auger within a conveyor housing of an auger conveyor.

In the illustrated embodiment, the intermediate outlet 44 comprises a plurality of outlet openings 52 at circumferentially spaced apart locations evenly about a circumference of the conveyor housing 32. A suitable gate 54 is provided in the form of an annular collar which is slidably mounted on the conveyor housing so that an interior diameter of the collar closely matches an exterior diameter of the housing. The gate 54 is slidable longitudinally along the conveyor housing between a closed position and an open position, in which the gate 54 is displaced upwardly in the open position relative to the closed position. In the closed position, the cover fully spans across and closes the outlet openings 52 defining the intermediate outlet 54 such that any material conveyed by the auger conveyor is directed upwardly past the intermediate outlet to be fully discharged through the distal outlet 46. In the open position, the collar is spaced upwardly from the closed position so that the outlet openings 52 are fully or partially unobstructed by the collar so as to result in a combined exposed area of the outlet openings defining the intermediate outlet being sufficient to discharge all of the conveyed material therethrough according to the first mode of operation of the auger conveyor.

One or more intermediate discharge chutes 56 are mounted on the conveyor housing 32 such that each discharge chute is aligned with a respective one of the outlet openings 52 to be sloped downwardly and radially outward therefrom by a radial distance which is considerably less than a radius of the storage bin. The discharge chutes are sloped downwardly at a slope which is sufficiently near vertical to prevent accumulation of any material thereon and thus allows discharge of material therethrough by action of gravity alone. In the open position of the gate 54, all material conveyed by the auger is discharged through the outlet openings 52 of the intermediate outlet 44 to be deposited into respective ones of the intermediate discharge chutes 56 which evenly disperse the discharged grain within the annulus between the conveyor housing 32 and the surrounding cylindrical boundary wall 28 of the first storage bin.

The gate 54 may be manually displaced between open and closed positions corresponding to first and second modes of operation of the auger conveyor respectively by a winch assembly that includes a winch mechanism 58 for winding a cable thereon, a winch cable 60 and a plurality of pulleys 62 supported on the conveyor housing 32 to guide the winch cable to extend from the mechanism 58 mounted externally on the first storage bin 12 near the bottom thereof to the collar forming the gate 54 at the top end of the first storage bin. The cable can communicate through the top wall of the storage bin through a suitable opening that is configured to prevent entry of precipitation into the storage bin in a similar manner to the top wall 30 being sealed relative to the conveyor housing 32 that also extends upwardly through the top end of the first storage bin. In this manner, an operator that manually operates the winch mechanism 58 causes the cable to be wound onto the winch mechanism which in turn causes the gate 54 to be raised from the closed position to the open position. Releasing the winch mechanism may allow the gate 54 to close by gravity, or alternatively an additional winch cable may be further configured to operate the gate 54 in the reverse orientation to lower the gate from the open position to the closed position thereof.

The auger conveyor 16 is driven to rotate in a consistent manner by the drive motor 50 for conveying material longitudinally upward through the conveyor housing from the intake that receives material from the bottom of the first storage bin 12 therein regardless of the operation of the auger conveyor in the first or second modes of operation.

In the first mode of operation, the auger conveyor operates to recycle the grain within the first storage bin by opening the gate member 54 so that all conveyed material is discharged through the intermediate outlet 44 defining the first discharge outlet of the auger conveyor. In this instance, grain is gathered from the bottom end of the first storage bin and discharged into the top end of the first storage bin in a continuing cycle.

In the second mode of operation, the auger conveyor operates to transfer grain from the first storage bin to the second storage bin by closing the gate member 54 so that all conveyed material is discharged through the distal outlet 46 defining the second discharge outlet of the auger conveyor. In this instance, grain is gathered from the bottom end of the first storage bin and discharge into the top end of the second storage bin and can continue to do so until the first storage bin has been substantially emptied and/or the second storage bin has been filled.

The apparatus 10 includes an ozone generator 64 capable of generating ozone to define a source of ozone in proximity to the first storage bin. The ozone injector 18 comprises an injector line communicating from the ozone generator 64 through a boundary of the first storage bin and into the conveyor housing 32 of the auger conveyor adjacent to the intake opening at the bottom end thereof. Suitable valves are provided in communication with the injector line defining the ozone injector 18 to control when ozone is injected into the auger conveyor and the rate of injection of the ozone according to the conveying rate of the auger conveyor 16. The ozone injector 18 is activated to inject ozone into the conveyor housing while the auger conveyor is operating to convey grain longitudinally therethrough such that the injected ozone mixes with and treats the grain being conveyed. The ozone injector 18 can be operated to inject ozone into the auger conveyor when the auger conveyor is operating in either one or both of the first mode or second mode of operation thereof.

The first recycling mode of operation can be used to increase the amount of exposure of the grain to the ozone.

The second transfer mode can be used to discharge the grain from the first storage bin subsequent to the first recycling mode to expose the grain to a second treatment with ozone or to simply transfer the grain to the second storage bin if no further treatment is required for example as indicated by testing of the grain.

Since various modifications can be made in my invention as herein above described, and many apparently widely different embodiments of same made, it is intended that all matter contained in the accompanying specification shall be interpreted as illustrative only and not in a limiting sense.

The invention claimed is:

1. A treatment apparatus for treating grain with ozone from a source of ozone, the apparatus comprising:
   a first storage bin arranged to contain a first portion of the grain therein;
   a second storage bin in proximity to the first storage bin, the second storage bin being arranged to contain a second portion of the grain therein;
   an auger conveyor arranged to convey the grain longitudinally through the auger conveyor from a first end to a second end of the auger conveyor, the first end of the auger conveyor being in communication with a bottom end of the first storage bin to receive the grain into the first end of the auger conveyor from the first storage bin; and
   an ozone injector arranged to inject ozone from the ozone source into the auger conveyor such that the grain conveyed by the auger conveyor is treated by the ozone;
   the auger conveyor including a first discharge outlet in association therewith, the first discharge outlet being in communication with the first storage bin adjacent a top end of the first storage bin;
   the auger conveyor including a second discharge outlet in association therewith, the second discharge outlet being in communication with the second storage bin adjacent a top end of the second storage bin;
   the auger conveyor being selectively operable in either one of a first mode or a second mode;
   in the first mode, the auger conveyor being arranged to discharge the grain through the first discharge outlet into the first storage bin; and
   in the second mode, the auger conveyor being arranged to discharge the grain through the second discharge outlet into the second storage bin.

2. The apparatus according to claim 1 wherein the first end of the auger conveyor is supported within the first storage bin.

3. The apparatus according to claim 1 wherein the first storage bin comprises a hopper bottom having a sloped bottom wall tapering towards a central discharge gate, the first end of the auger conveyor being located within a boundary of the sloped bottom wall of the hopper bottom at a location spaced above the central discharge gate of the hopper bottom.

4. The apparatus according to claim 1 wherein the auger conveyor extends longitudinally through the top end of the first storage bin from the first end of the auger conveyor within the first storage bin to the second end of the auger conveyor above the first storage bin.

5. The apparatus according to claim 1 wherein the ozone injector is in communication with the auger conveyor at an intermediate location nearer to the first end than the second end of the auger conveyor.

6. The apparatus according to claim 1 wherein the ozone injector is in communication with the auger conveyor in proximity to the first end of the auger conveyor.

7. The apparatus according to claim 1 wherein the auger conveyor is driven by an auger motor supported at the second end of the auger conveyor, externally of the first and second storage bins.

8. The apparatus according to claim 1 wherein one of the discharge outlets comprises an intermediate outlet at an intermediate location spaced from the second end of the auger conveyor and one of the discharge outlets comprising a distal outlet at the second end of the auger conveyor.

9. The apparatus according to claim 8 wherein the auger conveyor includes a gate operable relative to the intermediate outlet between a closed position blocking the intermediate outlet so as to discharge the grain through the distal outlet according to one of the modes of the auger conveyor and an open position allowing discharge of grain through the intermediate outlet according to another one of the modes of the auger conveyor.

10. The apparatus according to claim 9 wherein the auger conveyor comprises:
    a conveyor housing;
    a conveyor auger rotatably supported within the conveyor housing to convey the grain along the conveyor housing;
    the intermediate outlet comprising one or more outlet openings formed in the conveyor housing; and
    the gate comprising a collar supported for sliding movement relative to the conveyor housing between the closed position spanning across the one or more outlet openings in the conveyor housing and the open position in which the one or more outlet openings are at least partly unobstructed by the collar.

11. The apparatus according to claim 8 wherein the intermediate outlet is the first discharge outlet in communication with the first storage bin and the distal outlet is the second discharge outlet in communication with the second storage bin.

12. The apparatus according to claim 11 wherein the first discharge outlet is situated within an interior of the first storage bin.

13. The apparatus according to claim 1 further comprising a discharge chute arranged to discharge grain therethrough by gravity from the second discharge outlet to the top end of the second storage bin.

14. The apparatus according to claim 1 further comprising a discharge chute arranged to discharge grain therethrough by gravity from the first discharge outlet to the top end of the first storage bin.

* * * * *